(12) United States Patent
Reschke et al.

(10) Patent No.: US 8,491,617 B2
(45) Date of Patent: *Jul. 23, 2013

(54) LOW PROFILE CUTTING ASSEMBLY WITH A RETURN SPRING

(75) Inventors: Arlen J. Reschke, Longmont, CO (US); Daniel A. Joseph, Golden, CO (US); Paul R. Romero, Loveland, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/453,336

(22) Filed: Apr. 23, 2012

(65) Prior Publication Data

US 2012/0215242 A1  Aug. 23, 2012

Related U.S. Application Data (63) Continuation of application No. 12/556,025, filed on Sep. 9, 2009, now Pat. No. 8,162,965.

(51) Int. Cl.
*A61B 17/32* (2006.01)
*A61B 17/285* (2006.01)

(52) U.S. Cl.
USPC .......................................... 606/167; 606/205

(58) Field of Classification Search
USPC ............. 606/51, 52, 167, 170, 174, 205–211; 600/562–572
See application file for complete search history.

(56) References Cited

U.S. PATENT DOCUMENTS

| | | | |
|---|---|---|---|
| 4,278,089 A | 7/1981 | Huck et al. | |
| 4,534,351 A | 8/1985 | Rothfuss et al. | |
| 4,807,347 A | 2/1989 | Johnson | |
| 4,863,429 A | 9/1989 | Baldwin | |
| 5,427,088 A * | 6/1995 | Graether ...................... | 600/236 |
| 5,462,558 A | 10/1995 | Kolesa et al. | |
| 5,478,316 A | 12/1995 | Bitdinger et al. | |
| 5,709,662 A | 1/1998 | Olive et al. | |
| 5,779,647 A | 7/1998 | Chau et al. | |
| 5,938,667 A | 8/1999 | Peyser et al. | |

(Continued)

FOREIGN PATENT DOCUMENTS

| | | |
|---|---|---|
| CA | 2104423 | 2/1994 |
| DE | 2415263 | 10/1975 |

(Continued)

OTHER PUBLICATIONS

US. Appl. No. 12/336,970, filed Dec. 17, 2008.

(Continued)

*Primary Examiner* — Kathleen Holwerda (57) ABSTRACT

The present disclosure relates to a forceps that includes a housing, a cutting assembly, and an actuator. The housing has a shaft attached thereto that extends therefrom and is configured to support a pair of jaw members at a distal end thereof. The jaw members are movable to grasp tissue therebetween. The cutting assembly includes a spring element that has proximal and distal ends. The proximal end of the spring element is fixed to a boss disposed within the housing and the distal end of the spring element includes a cutting edge. The spring element is coiled at a proximal end thereof to create a spring bias against the boss. The actuator is operably coupled to the spring element and is configured to selectively advance the cutting edge of the spring element into the jaw members against the spring bias to sever tissue disposed therebetween.

19 Claims, 4 Drawing Sheets

U.S. PATENT DOCUMENTS

| | | | |
|---|---|---|---|
| 6,010,519 A | 1/2000 | Mawhirt et al. | |
| 6,032,849 A | 3/2000 | Mastri et al. | |
| 6,146,399 A * | 11/2000 | Lee | 606/167 |
| 7,131,970 B2 | 11/2006 | Moses et al. | |
| 7,252,667 B2 | 8/2007 | Moses et al. | |
| 8,162,965 B2 * | 4/2012 | Reschke et al. | 606/167 |
| 2004/0089759 A1 | 5/2004 | Genuise | |
| 2005/0119655 A1 | 6/2005 | Moses et al. | |
| 2005/0154387 A1 | 7/2005 | Moses et al. | |
| 2006/0079877 A1 | 4/2006 | Houser et al. | |
| 2006/0079891 A1 | 4/2006 | Arts et al. | |
| 2007/0088356 A1 | 4/2007 | Moses et al. | |
| 2008/0319442 A1 | 12/2008 | Unger et al. | |

FOREIGN PATENT DOCUMENTS

| | | |
|---|---|---|
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |
| GB | 623316 | 5/1949 |
| GB | 1490585 | 11/1977 |
| GB | 2214430 | 6/1989 |
| GB | 2213416 | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |

OTHER PUBLICATIONS

U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Wed in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surgery, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al, "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999. vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185:1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

LOW PROFILE CUTTING ASSEMBLY WITH A RETURN SPRING

CROSS-REFERENCE TO RELATED APPLICATIONS

The present application claims the benefit of and priority to U.S. patent application Ser. No. 12/556,025, filed Sep. 9, 2009, now U.S. Pat. No. 8,162,965, the contents of which is incorporated by reference herein in its entirety for all purposes.

BACKGROUND

1. Technical Field

The present disclosure relates to surgical instruments. More particularly, the present disclosure relates to surgical instruments having sealing and cutting capabilities.

2. Description of Related Art

During a typical surgical procedure, for example, an open or endoscopic electrosurgical procedure, a clinician may in certain circumstances have to remove an electrosurgical instrument from an operative site, substitute a new instrument, and accurately sever a vessel, which was previously electrosurgically treated. As can be appreciated, this additional step may be both time consuming (particularly when treating multiple operative sites) and may contribute to imprecise separation of the tissue due to the misalignment or misplacement of the severing instrument along the previously electrosurgically treated tissue.

Many surgical instruments have been designed which incorporate a knife or blade member that effectively severs the tissue after an electrosurgical procedure has been performed. For example, commonly-owned U.S. Pat. Nos. 7,083,618 and 7,101,371 describe one such electrosurgical instrument that effectively seals and cuts tissue along the formed tissue seal. Other instruments include blade members or shearing members which simply cut tissue in a mechanical and/or electromechanical manner and are relatively ineffective for electrosurgical procedures.

SUMMARY

The present disclosure relates to a forceps that includes a housing, a cutting assembly, and an actuator. The housing has a shaft attached thereto that extends therefrom and is configured to support a pair of jaw members at a distal end thereof that are movable to grasp tissue therebetween. The cutting assembly includes a spring element with proximal and distal ends; the proximal end of the spring element is fixed to a boss disposed within the housing and the distal end of the spring element includes a cutting edge. The spring element is coiled at a proximal end thereof to create a spring bias against the boss. The spring element may be made from spring steel or plastic. The actuator is operably coupled to the spring element and is configured to selectively advance the cutting edge of the spring element into the jaw members against the spring bias to sever tissue disposed therebetween.

In some embodiments, a cutting element may be attached to the distal end of the spring element and extend therefrom. The cutting edge may be defined by the cutting element at a distal end thereof. The spring element may be biased against the boss with a constant force. The boss may be bifurcated to define a slit therebetween to secure the spring element thereto. The proximal end of the spring element may be secured to the boss by a fastening technique, for example, crimping, welding, gluing, over-molding, or friction-fitting.

In some embodiments, one or more stops may be operably coupled to the forceps within the housing. The stops may include a slot defined therethrough configured to receive the spring element. The cutting assembly may also include one or more bumpers that may be operably coupled to the spring element. The bumpers may cooperate with the stops to limit movement of the spring element to within a predetermined range.

The present disclosure also relates to a forceps including a housing, a cutting assembly, and an actuator. The housing has a shaft attached thereto that extends therefrom and is configured to support a pair of jaw members at a distal end thereof that are movable to grasp tissue therebetween. The cutting assembly includes a spring element, a joining member, and a cutting element. The spring element with proximal and distal ends; the proximal end of the spring element is fixed to a boss that is disposed within the housing. The spring element is coiled at a proximal end thereof to create a spring bias against the boss. The joining member is disposed between the proximal and distal ends of the spring element and configured to receive and secure the spring element. The cutting element is attached to a distal end of the joining member and extends therefrom. The cutting element includes a cutting edge defined at a distal end thereof. The actuator is operably coupled to the spring element and configured to selectively advance the joining member against the bias of the spring element which, in turn, advances the cutting edge of the cutting element to sever tissue disposed between the jaw members.

In some embodiments, a guide pin may be disposed within the housing of the forceps. The guide pin may be configured to support the spring element at least partially therearound to substantially reverse the actuation direction for advancing the cutting edge of the cutting element. The guide pin may include a pulley that facilitates actuation of the spring element against the spring bias.

BRIEF DESCRIPTION OF THE DRAWINGS

Various embodiments of the subject instrument are described herein with reference to the drawings wherein.

DETAILED DESCRIPTION

Embodiments of the presently-disclosed electrosurgical instrument are described in detail with reference to the drawings wherein like reference numerals identify similar or identical elements. As used herein, the term "distal" refers to that portion which is further from a user while the term "proximal" refers to that portion which is closer to a user.

In general, the present disclosure relates to a cutting assembly that is utilized in conjunction with surgical instruments. The cutting assembly may include a constant force spring element and a cutting element that defines a cutting edge at a distal end thereof. The constant force spring element includes fixed and movable ends. The fixed end of the spring element is configured in a biasing coiled configuration. During use, the movable end is selectively moved from a first position to a second position in order to cut tissue. After a successful cut has been performed, the movable end of the spring element is selectively released, which, in turn, retracts the movable end from the second position to the initial first position due to the biasing force of the spring. As can be appreciated, the incorporation of a spring element and a cutting element into a unitary composition, such as one-piece configuration facilitates the manufacturing and assembly process. More particularly, having a unitary composition is beneficial, since less components are used, which in turn, reduces assembly time, reduces manufacturing costs, reduces the amount of components being utilized, and is less prone to failure.

Figure 1A:
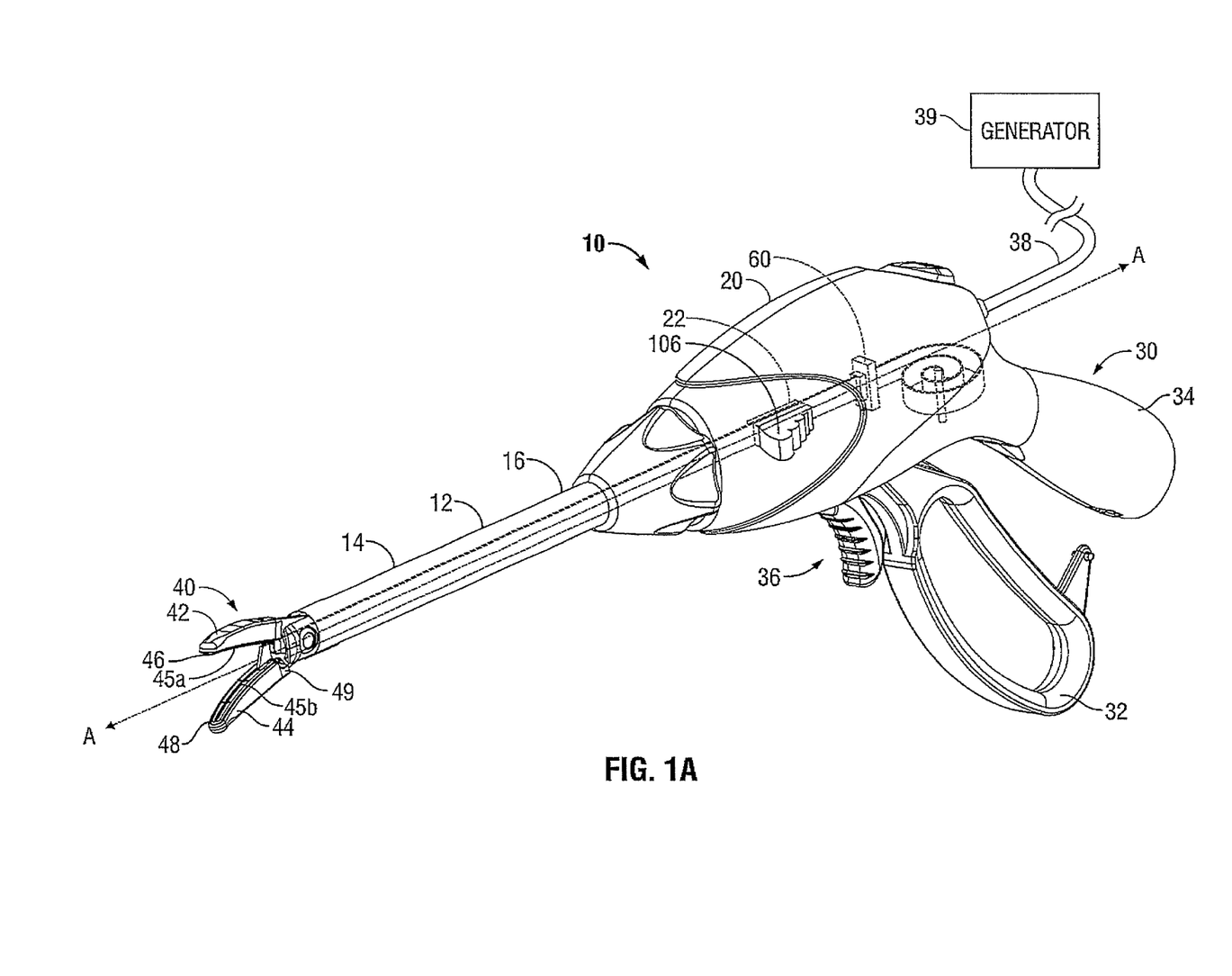
FIG. 1A is an internal, perspective view of an endoscopic forceps showing a cutting assembly in accordance with an embodiment of the present disclosure.
Figure 1B:
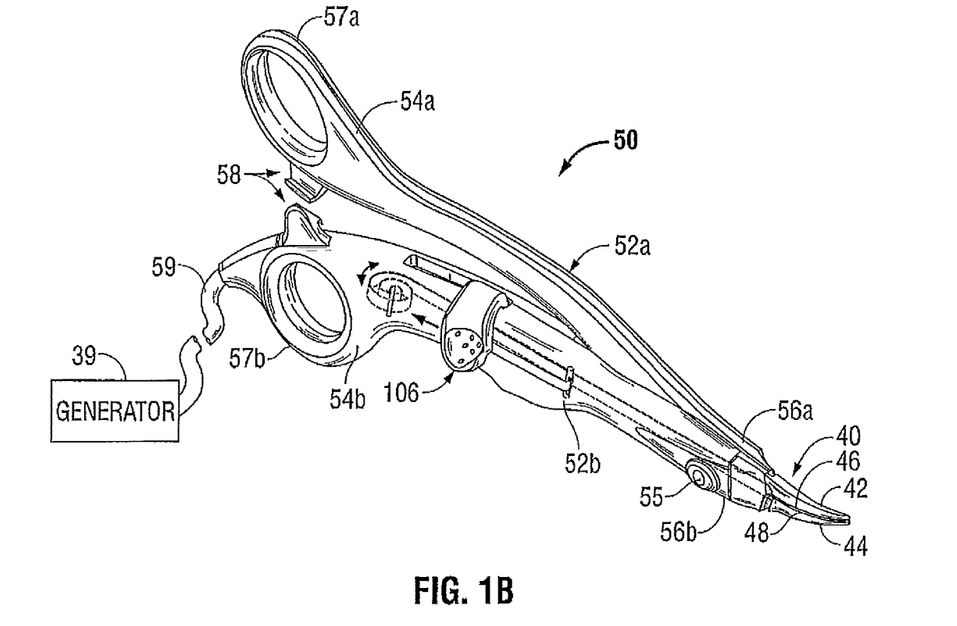
FIG. 1B is an internal, perspective view of an open forceps showing the cutting assembly in accordance with another embodiment according to the present disclosure.

Referring now to the figures, FIG. 1A depicts a forceps 10 used in correlation with endoscopic surgical procedures and FIG. 1B depicts an open forceps 50 used in correlation with more traditional open surgical procedures. For the purposes herein, either an endoscopic instrument or an open instrument may be utilized with the cutting assembly described herein. It should be noted that different electrical and mechanical connections and considerations apply to each particular type of instrument. However, the novel aspects, with respect to the cutting assembly and its operating characteristics, remain generally consistent with respect to both the endoscopic or open designs.

Turning now to FIG. 1A, a forceps 10 is shown for use with various endoscopic surgical procedures and generally includes a housing 20, a handle assembly 30, an end effector assembly 40 and a cutting assembly 100. The end effector assembly 40 includes opposing jaw members 42 and 44 that mutually cooperate to grasp, seal and/or divide tubular vessels, vascular tissue, or any other suitable tissue. The opposing jaw members 42 and 44 include sealing plates 46 and 48 (also referred to, throughout the description, as sealing plates, sealing electrodes, or tissue contacting plates) and knife channels 45a and 45b defined therein, which will be further described below. Forceps 10 includes a shaft 12 that has a distal end 16 dimensioned to mechanically engage the end effector assembly 40 and a proximal end 14 that mechanically engages the housing 20. The shaft 12 may include one or more known mechanically engaging components that are designed to securely receive and engage the end effector assembly 40 such that the jaw members 42 and 44 are pivotable relative to one another to engage and grasp tissue therebetween.

Handle assembly 30 includes a fixed handle 34 and a movable handle 32. Fixed handle 34 is integrally associated with housing 20 and handle 32 is movable relative to fixed handle 34 to actuate the opposing jaw members 42 and 44 of the end effector assembly 40. Handle assembly 30 further includes a cable 38 that connects the forceps 10 to a source of electrosurgical energy, e.g., an electrosurgical generator 39. Cable 38 is internally divided within the handle assembly 30 and the shaft 12 to transport electrosurgical energy through various conductive paths and ultimately to end effector assembly 40.

As mentioned above, the end effector assembly 40 is positioned on the distal end 16 of shaft 12 and includes the opposing jaw members 42 and 44. Movable handle 32 of the handle assembly 30 translates movement of the jaw members 42 and 44 from an open position (also referred to as a first position), such that the jaw members 42 and 42 are disposed in spaced relation relative to one another to a clamped or closed position (also referred to as a second position), such that the jaw members 42 and 44 cooperate to grasp tissue therebetween.

Referring now to FIG. 1B, an open forceps 50 is depicted and includes end effector assembly 40 (similar to forceps 10) that is attached to a pair of elongated shaft portions 52a and 52b. Elongated shaft portions 52a and 52b have proximal ends 54a and 54b and distal ends 56a and 56b, respectively. The end effector assembly 40 includes jaw members 42 and 44 that attach to distal ends 56a and 56b of shafts 52a and 52b, respectively. The jaw members 42 and 44 are connected about pivot pin 55 that allows the jaw members 42 and 44 to pivot relative to one another from the first to second positions for treating tissue (as described above). Seal plates 46 and 48 are connected to opposing jaw members 42 and 44 and include electrical connections through or around the pivot pin 55.

Each shaft 52a and 52b includes a handle 57a and 57b disposed at the proximal end 54a and 54b thereof. Handles 57a and 57b facilitate movement of the shafts 52a and 52b relative to one another which, in turn, pivot the jaw members 42 and 44 from the open position wherein the jaw members 42 and 44 are disposed in spaced relation relative to one another to the clamping or closed position wherein the jaw members 42 and 44 cooperate to grasp tissue therebetween.

In an example embodiment, as depicted in FIG. 1B, a ratchet 58 is included for selectively locking the jaw members 42 and 44 relative to one another at various positions during pivoting. The ratchet 58 is configured to hold a specific, i.e., constant, strain energy in the shaft members 52a and 52b which, in turn, transmits a specific closing force to the jaw members 42 and 44. It is envisioned that the ratchet 58 may include graduations or other visual markings that enable the user to easily and quickly ascertain and control the amount of closure force desired between the jaw members 42 and 44.

With continued reference to FIG. 1B, forceps 50 is depicted having a cable 59 that connects the forceps 50 to a source of electrosurgical energy, e.g., electrosurgical generator 39. In a similar fashion to forceps 10, cable 59 of forceps 50 is internally divided within the shaft 52b to transmit electrosurgical energy through various electrical conductive paths to the components of the end effector assembly 40.

Figure 2:
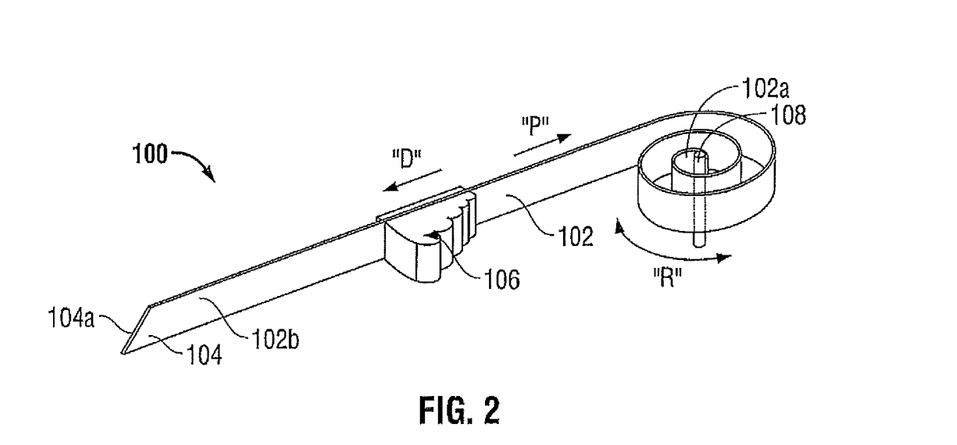
FIG. 2 is an enlarged, perspective view of one embodiment of the cutting assembly in accordance with the present disclosure showing a constant force spring element at a proximal end thereof and a knife at a distal end thereof.

Referring now to FIG. 2, a cutting assembly in accordance with the present disclosure is generally shown as cutting assembly 100. Cutting assembly 100 includes a constant force spring element 102, a cutting element 104, and a finger actuator 106. The cutting assembly 100 is disposed within forceps 10 or 50 such that a user may selectively actuate the cutting assembly 100 to cut vascular tissue (or any other suitable tissue). The cutting assembly 100, and the various embodiments that will be described in greater detail below, may be utilized and installed into any suitable type of surgical instrument and not limited to the surgical instruments described herein.

Spring element 102 is made of a strip or band of material, for example, but not limited to, spring steel or plastic, and includes a fixed end 102a and a movable end 102b. Spring element 102 may be made from any suitable material, so long as it is durable (i.e., will not easily break). For example, spring element 103 may also be made of shape memory metal or bimetallic metal.

In the illustrated embodiment, the fixed end 102a of spring element 102 is rolled into a coil-like biasing configuration with a varying radial diameter "R," and is secured to a boss 108 (or pin) by any suitable attaching means, for example, but not limited to, crimping, welding, gluing, over-molding, or friction-fitting. Any number of coils may be utilized depending upon a particular purpose. Spring element 102 may be configured into any suitable shape, for example, but not limited to spiral, coil, helical, and conical. The movable end 102b of spring element 102 includes a cutting element 104 at a distal end thereof that defines a cutting edge 104a configured to cut and/or sever tissue held between the jaw members 42 and 44. The spring element 102 also includes an actuator assembly 106, which may be, for example, a finger actuating assembly, as shown in FIG. 2 and as described in further detail below.

The specific forces required for spring element 102 to cut and/or sever tissue are determined by the type, size, and/or shape of the jaw members 42 and 44. For example, a spring element having a two pound (2*lb*) retraction force may be suitable for a 7 mm curved jaw configuration. In other configurations, for example, a 3 mm straight jaw configuration, a spring element may require a substantially less retraction force. In essence, the higher retraction force a spring element 102 contains, the greater actuation force is necessary to actuate cutting element 104. In substantially delicate procedures, a lower retraction and actuation force of a spring element may be suitable, since cutting delicate tissue does not require a great force and a low actuation force would give a clinician greater control.

In some embodiments, the actuator assembly 106 may include suitable mechanical linkage such that a trigger assembly 36 (as shown in FIG. 1A) or any other mechanical mechanism, e.g., a motor or a lever, may be connected thereto. The movable end 102b is configured for selective movement from a first position, most proximal position, to a second position in a distal direction "D" to advance the cutting edge 104a through tissue via the actuator assembly 106. When the movable end 102b is selectively released, the coiled configuration of the fixed end 102a biasingly retracts the movable end 102b in a second direction, for example, in a proximal direction "P," such that cutting element 104 is retracted from the second position to the first position. Fixed end 102a may be coupled to a separate retracting mechanism such that the spring element 102 is not limited to only materials that have resilient characteristics.

Figure 3:
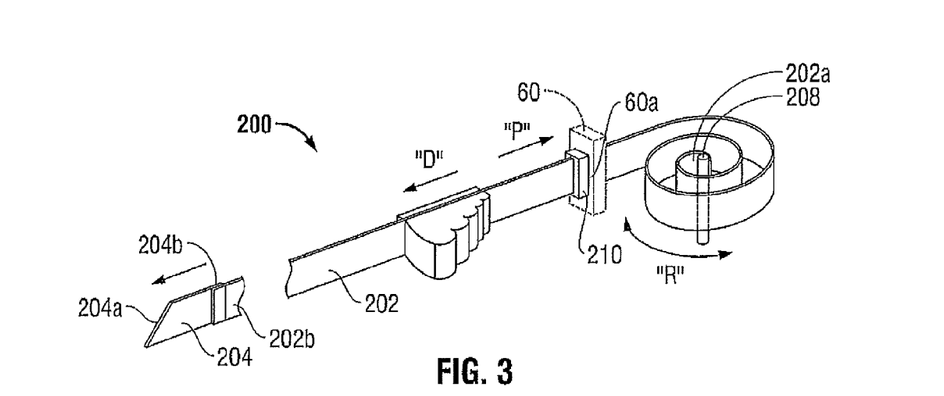
FIG. 3 is an enlarged, perspective view of another embodiment of the cutting assembly in accordance with the present disclosure showing a mechanical stop or bumper for limiting proximal movement of the cutting element.

FIG. 3 illustrates another embodiment of a cutting assembly 200 that is similar to cutting assembly 100 and includes a spring element 202, a cutting element 204, and a finger actuator 206. Cutting assembly 200 also includes a bumper 210 and separate spring and cutting elements 202 and 204, respectively. More particularly, spring element 202 is made from spring steel (or plastic) and includes a fixed end 202a and a movable end 202b. The fixed end 202a of spring element 202 is rolled into a coil-like biasing configuration with a varying radial diameter "R," and is secured to a boss 208 by any suitable attaching means, for example, but not limited to, crimping, welding, gluing, over-molding, or friction-fitting. Any number of coils may be utilized depending upon a particular purpose. The movable end 202b of spring element 202 includes a cutting element 204 at a distal end thereof that defines a cutting edge 204a configured to cut and/or sever tissue held between the jaw members 42 and 44. The spring element 202 also includes an actuator assembly 206, which may be, for example, a finger actuating assembly, as shown in FIG. 2 and as described in further detail below.

In some embodiments, the actuator assembly 206 may include one or more mechanical linkages such that a trigger assembly 36 (as shown in FIG. 1A) or any other mechanical powering mechanism, e.g., a motor, may be connected thereto. The movable end 202b is configured for selective movement from a first position, most proximal position, to a second position in a distal direction "D" to advance the cutting edge 204a through tissue via the actuator assembly 206. When the movable end 202b is selectively released, the coiled configuration of the fixed end 202a biasingly retracts the movable end 202b in a second direction, for example, in a proximal direction "P," such that cutting element 204 is retracted from the second position to the first position. Fixed end 202a may be coupled to a separate retracting mechanism such that the spring element 202 is not limited to only materials that have resilient characteristics.

Bumper 210 is disposed along the length of the spring element 202 and is mechanically coupled by any of the above-mentioned suitable attaching techniques. Bumper 210 is configured to prevent cutting assembly 200 from moving proximally "P" past a predetermined position. In an example embodiment, as shown in FIG. 3, a stop 60 may be positioned at a predetermined position and along the length of cutting assembly 200 such that the bumper 210 abuts the stop 60 at a predetermined position. In some embodiments, stop 60 may be operably coupled to the forceps within the housing and may include a slot 60a defined therethrough to receive the spring element 202.

Figure 4:
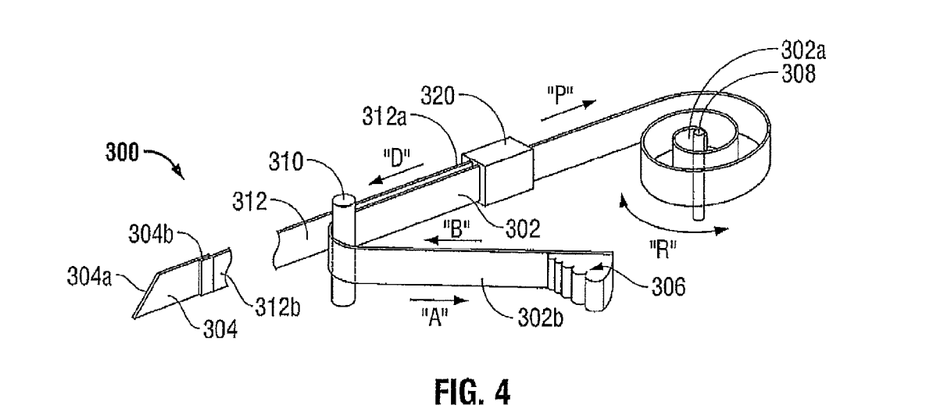
FIGS. 4-6 are a enlarged, perspective views of other embodiments of the cutting assembly in accordance with the present disclosure wherein the actuating element is offset from the cutting assembly.

FIG. 4 depicts another embodiment of a cutting assembly that resembles cutting assembly 100 and includes a spring element 302, a cutting element 304, and a finger actuator 306. Cutting assembly 300 also includes a support element 312 that has a proximal end 312a and a distal end 312b.

Spring element 302 is made of a strip or band of material such as spring steel or plastic, and has a fixed end 302a and a movable end 302b. The fixed end 302a of spring element 302 is rolled into a coil-like biasing configuration with a varying radial diameter "R," and is secured to a boss 308 by any suitable attaching means, for example, but not limited to, crimping, welding, gluing, over-molding, or friction-fitting.

A proximal end 304b of cutting element 304 is coupled to the distal end 312b of the support element 312 by any of the above-mentioned suitable attaching techniques. The proximal end 312a of the support member 312 is affixed to a joining member 320 that couples the spring element 302 with the support member 312. Joining member 320 may be coupled to the portion of spring element 302 by any suitable attaching technique. On a distal end of the cutting element 304, a cutting edge 304a is defined and configured to cut and/or sever tissue held between the jaw members 42 and 44. In this configuration, as the portion of the spring element 302 is moved in a distal direction "D" both the joining member 320 and the spring element 302 move correspondingly in the distal direction "D." Movable end 302b of spring element 302 includes actuator assembly 306 (e.g., a finger actuating assembly).

With continued reference to FIG. 4, the cutting assembly 300 includes a guide pin 310 that guides the spring element 302 (e.g., in a looping manner) in a direction "A," which is offset at an angle with respect to the direction "D." Direction "A" may be equivalent or substantially equivalent to proximal direction "P." In this manner, the movable end 302b of spring element 302 is configured to selectively move the portion of the spring element 302, which, in turn, selectively moves both the joining member 320 and the spring element 302.

When the movable end 302b is selectively released, the coil-like biasing configuration of the fixed end 302a retracts the movable end 302b in a direction "B," which is opposite direction "A," such that cutting element 304 is retracted from the second position to the first position.

Joining member 320 may also act as a bumper, as described above, with regard to bumper 210. In this manner, joining member 320 may be configured to prevent cutting assembly 300 from moving in a proximal direction "P" past a predetermined position.

Figure 5:
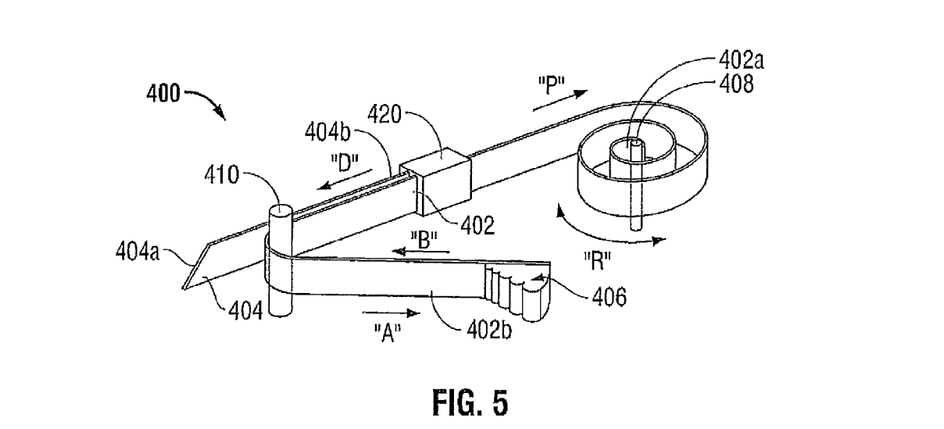

FIG. 5 depicts another embodiment of a cutting assembly 400 that is similar to cutting assembly 300 such that it includes a spring element 402, a cutting element 404, an actuator assembly 406, and a joining member 420. The cutting element 404 is attached to the joining member and similar to cutting elements 104, 204, and 304, cutting element 404 defines a cutting edge 404a that is configured to cut and/or sever tissue held between the jaw members 42 and 44.

A proximal end 404b of cutting element 404 is coupled to the joining member 420, which, in turn, is joined and coupled to a portion of spring element 402 between fixed and movable ends 402a and 402b. Joining member 420 may be coupled to the portion of spring element 402 by any suitable attaching technique. In this configuration, as the portion of the spring element 402 is moved from a first position, in a distal direction "D" both the joining member 420 and the spring element 402 move in the distal direction "D." Movable end 402b of spring element 402 includes actuator assembly 406 (e.g., a finger actuating assembly).

With continued reference to FIG. 5, the cutting assembly 400 also includes a pin 410 that guides the spring element 402 (e.g., in a looping manner) in a direction "A," which is offset at an angle with respect to the direction "D." Direction "A" may be equivalent or substantially equivalent to proximal direction "P." In this manner, the movable end 402b of spring element 402 is configured to selectively move the portion of the spring element 402, which, in turn, selectively moves both the joining member 420 and the spring element 402.

When the movable end 402b is selectively released, the coil-like biasing configuration of the fixed end 402a retracts the movable end 402b in a direction "B," which is opposite direction "A," such that cutting element 404 is retracted from the second position to the first position.

Figure 6:
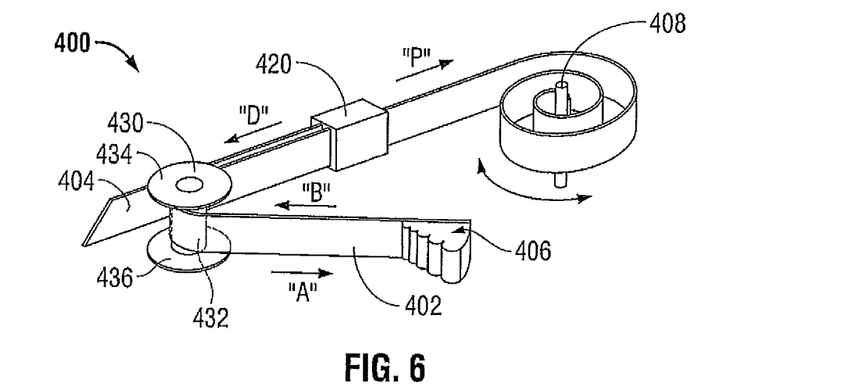

As best shown in FIG. 6, a pulley 430 may be utilized with the above-described cutting assemblies 100, 200, 300, and 400. Pulley 430 may include a shaft 432 and first and second guides 434 and 436, respectively that are configured to contain the spring element 402 therewithin. Pulley 430 may also include low-friction ball bearings such that pulley 430 may turn substantially frictionless as the spring element 402 is moved along pulley 430. In other words, the pulley 430 facilitates actuation of the spring element 402 against the spring bias. It should be noted that other types of devices or mechanisms may be used to facilitate guiding the spring element 402.

Figure 7:
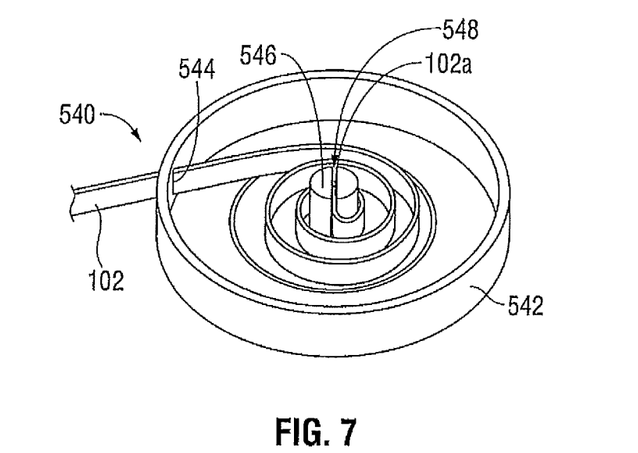
FIG. 7 is a greatly-enlarged, perspective view of a spring housing of the cutting assembly that is utilized with the present disclosure.

FIG. 7 depicts an example embodiment of a spring housing assembly 540 that includes a housing 542, which may be covered by a cover (not shown). The housing 542 includes a bifurcated pin 546 having a slit 548 defined therethrough such that the fixed end 102a of the spring element 102 may be secured within the slit 548 at a fixed position. The remaining portion of the spring element 102 is curled around pin 546 around itself to secure the spring element 102 in place.

Figure 8:
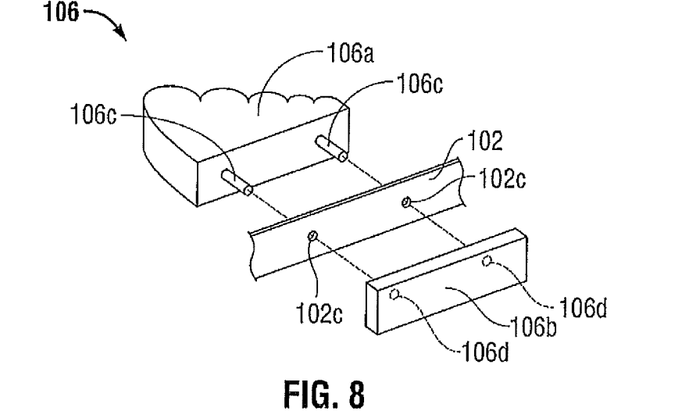
FIG. 8 is a greatly-enlarged, exploded view of a thumb actuator of the cutting assembly of the present disclosure.

FIG. 8 is an exploded view of actuator assembly 106 mounted onto a portion of spring element 102. In some embodiments the actuator assembly may include a first and second portion 106a and 106b, respectively, such that the first portion 106a defines one or more detents 106c and the second portion 106b has one or more corresponding receiving holes 106d that are configured to receive the one or more detents 106c of first portion 106a. The cutting assembly 102 also includes one or more holes 102c configured to receive and allow passage of the detents 106c therethrough. In this manner, detents 106c pass through the holes 102c such that first portion 106a mates with the second portion 106b sandwiching the cutting assembly 102 at a desired location.

During use, a user can actuate the cutting assembly simply by applying pressure to the finger actuator in any of the above-described embodiments. As described above, all of the cutting assembly embodiments are beneficial since they are simply constructed and contain very few components. For example, the spring element and the knife element of cutting assembly 100 may be made out of a single piece of material. It should be noted that any component of the above-described embodiments may be switched and utilized with any of the other embodiments.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    at least one shaft configured to support a pair of jaw members at a distal end thereof, the jaw members movable to grasp tissue therebetween;
    a cutting assembly including;
        a spring element having proximal and distal ends, the proximal end of the spring element being fixed, the spring element coiled and biased at the proximal end thereof; and
        a cutting edge integrally or attachably disposed on the distal end of the spring element;
    a finger actuator fixed to the spring element configured to selectively advance the cutting edge of the spring element into the jaw members against the spring bias to sever tissue disposed therebetween; and
    a guide pin, the guide pin configured to support the spring element at least partially therearound to substantially reverse the actuation direction for advancing the cutting edge of the cutting assembly.

2. The forceps according to claim 1, further comprising:
    a housing supporting the at least one shaft thereto and extending therefrom; and
    a boss disposed within the housing, wherein the proximal end of the spring element is fixed about the boss.

3. The forceps according to claim 2, wherein the spring element is biased against the boss with a constant force.

4. The forceps according to claim 2, wherein the proximal end of the spring element is secured to the boss by a fastening technique selected from the group consisting of crimping, welding, gluing, over-molding, and friction-fitting.

5. The forceps according to claim 2, further comprising:
    at least one stop operably coupled to the forceps within the housing, the at least one stop including a slot defined therethrough configured to receive the spring element; and
    at least one bumper operably coupled to the spring element, the at least one bumper cooperating with the stop to limit movement of the spring element to within a predetermined range.

6. The forceps according to claim 2, wherein the boss is bifurcated to define a slit therebetween, the slit configured to secure the spring element thereto.

7. The forceps according to claim 1, wherein the cutting assembly further comprises a cutting element, wherein the cutting edge is defined on or attached to the cutting element, wherein the cutting element is attached to the distal end of the spring element and extends therefrom.

8. The forceps according to claim 1, wherein the spring element is made from at least one of spring steel or plastic.

9. The forceps according to claim 1, wherein the proximal end of the spring element is fixed about a boss disposed within the at least one shaft.

10. A forceps, comprising:
- at least one shaft configured to support a pair of jaw members at a distal end thereof, the jaw members movable to grasp tissue therebetween;
- a cutting assembly including:
  - a spring element having proximal and distal ends, the proximal end of the spring element being fixed, wherein the spring element is coiled and biased at the proximal end thereof;
  - a joining member disposed between the proximal and distal ends of the spring element and configured to receive and secure the spring element; and
  - a cutting element attached to a distal end of the joining member and extending therefrom, the cutting element including a cutting edge defined at a distal end thereof;
- a finger actuator fixed to the spring element configured to selectively advance the cutting edge of the cutting element into the jaw members against the spring bias to sever tissue disposed therebetween; and
- a guide pin, the guide pin configured to support the spring element at least partially therearound to substantially reverse the actuation direction for advancing the cutting edge of the cutting element.

11. The forceps according to claim 10, further comprising:
- a housing supporting the at least one shaft thereto and extending therefrom; and
- a boss disposed within the housing, wherein the spring element is fixed about the boss.

12. The forceps according to claim 11, further comprising:
- at least one stop operably coupled to the forceps within the housing, the at least one stop including a slot defined therethrough configured to receive the spring element; and
- at least one bumper operably coupled to the spring element, the at least one bumper cooperating with the stop to limit movement of the spring element to within a predetermined range.

13. The forceps according to claim 11, wherein the spring element is biased against the boss with a constant force.

14. The forceps according to claim 11, wherein the boss is bifurcated to define a slit therebetween, the slit being configured to secure the spring element thereto.

15. The forceps according to claim 10, wherein the spring element is fixed about a boss disposed within the at least one shaft.

16. The forceps according to claim 10, further comprising:
- at least one stop operably coupled to the forceps within the at least one shaft, the at least one stop including a slot defined therethrough configured to receive the spring element; and
- at least one bumper operably coupled to the spring element, the at least one bumper cooperating with the stop to limit movement of the spring element to within a predetermined range.

17. The forceps according to claim 10, wherein the spring element is made from at least one of spring steel or plastic.

18. The forceps according to claim 10, wherein the finger actuator further comprises a first portion and a second portion.

19. The forceps according to claim 18, wherein the first portion defines one or more detents and the second portion defines one or more corresponding receiving holes.

* * * * *